US006489148B1

(12) United States Patent
Mansfield et al.

(10) Patent No.: US 6,489,148 B1
(45) Date of Patent: Dec. 3, 2002

(54) IMMUNOASSAY FOR EQUINE PROTOZOAL MYELOENCEPHALITIS IN HORSES

(75) Inventors: Linda S. Mansfield, Bath, MI (US); Alice J. Murphy, St. Johns, MI (US); Mary G. Rossano, Mason, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/569,434

(22) Filed: May 12, 2000

Related U.S. Application Data

(62) Division of application No. 09/156,954, filed on Sep. 18, 1998, now Pat. No. 6,153,394.

(51) Int. Cl.⁷ .......................... C12N 9/00; G01N 33/55; G01N 33/53; G01N 33/567; C12Q 1/04
(52) U.S. Cl. ...................... 435/183; 435/7.22; 435/7.2; 435/34; 435/7.1; 530/388.6; 436/518
(58) Field of Search ................. 435/7.1, 7.22, 435/7, 5, 7.5, 7.31; 436/518, 523, 528, 543, 183; 536/23.1

(56) References Cited

U.S. PATENT DOCUMENTS

| | | | | |
|---|---|---|---|---|
| 4,298,685 A | * | 11/1981 | Parikh et al. | 435/7.5 |
| 4,740,456 A | * | 4/1988 | Kuhn et al. | 435/7 |
| 4,977,079 A | * | 12/1990 | Nuzzolo et al. | 435/7.22 |
| 5,210,018 A | * | 5/1993 | Nuzzolo et al. | 435/7.22 |
| 6,344,337 B1 | * | 2/2002 | Mansfield et al. | 435/7.2 |

OTHER PUBLICATIONS

Granstrom, J.P. et al., "Equine protozoal myeloencephalites: antigen analysis of cultured Sarcocystis neurona merozoites" Journal Veterinary Diagnostic Investigation, vol. 5, pp. 88–90, 1993.*
Dubey, J.P., et al., J. Parasitol 77:212–218 (1991).
Marsh, A. E., et al., J. Am Ved Med Assoc 209:1907–1913 (1996).
Granstrom, D.E., et al., J. Ved Diag Invest 5:88–90 (1993).
Fenger, C.K., et al., Vet Parasitol 68:199–213 (1997).
Bentz, B.G., et al., J. Am Vet Med Assoc 210:517–518 (1997).
Fenger, C.K., et al., J. Of Parasitology 81:916–919 (1995).
Conference of Research Workers in Animal Diseases—Abstract 162, Nov. 1997.
Hamir, A.N., et al., J. Vet Diagn Invest 5:418–422 (1993).
Saville, W. J., et al., JAVMA 210:519–524 (1997).
Blythe, L. L., et al. JAVMA 210:525–527 (1997).

* cited by examiner

Primary Examiner—Lynette R. F. Smith
Assistant Examiner—Khatol Shahnan-Shah
(74) Attorney, Agent, or Firm—Ian C. McLeod

(57) ABSTRACT

An immunoassay for *Sarcocystis neurons* antibodies in equines is described. The immunoassay uses blocking of Sarcocystis antigens by antibodies to Sarcocystis sp. other than *Sarcocystis neurona* in connection with the immunoassay.

13 Claims, 2 Drawing Sheets

=Genus (*Sarcocystis*)-specific antigen

=Species (*S. neurona*) - specific antigen

=Reagent for detecting labeled anti-equine IgG antibody

Equine IgG serum antibody

Labeled Anti-equine IgG antibody

Bovine anti-*S. cruzi* antibody

IMMUNOASSAY FOR EQUINE PROTOZOAL MYELOENCEPHALITIS IN HORSES

This application claims priority to divisional application Ser. No. 09/156,954, filed on Sep. 18, 1998, which has been patented now as U.S. Pat. No. 6,153,394.

BACKGROUND OF THE INVENTION

(1) Field of the Invention

The present invention relates to an immunoassay method and test kit for detecting antibodies to at least one protein of *Sarcocystis neurona* produced in an equine suspected of harboring the *Sarcocystis neurona* which causes myeloencephalitis in the equine. The disease is debilitating and may frequently be fatal. The preferred immunoassay method uses preblocking of a Western blot membrane containing at least one known identifying antigen of *Sarcocystis neurona* with unlabeled antibodies of a Sarcocystis sp. other than *Sarcocystis neurona* in order to prevent false positive, non-specific binding of a labeled antibody to the protein(s).

(2) Description of Related Art

A mammalian body reacts to the presence of foreign antigens by producing antibody molecules from its lymphocyte cells. Antibodies have the property of selectively binding to certain distinctive sites, known as determinants on antigens, thereby rendering the antigens innocuous. The antibodies have a physical affinity for specific determinants or epitopes of antigenic material. A reaction between an antibody and a determinant on an antigen for which the antibody is specific results in an adduct, commonly referred to as an "immunocomplex". The formation of such complexes makes possible a wide variety of assays for antigenic material. Such assays are known generically as immunoassays.

Immunoassays have replaced other procedures used for in vitro diagnostic methods to detect or quantitate a variety of antigens and/or antibodies in fluids and, particularly, body fluids such as blood serum, urine or spinal fluid with important biologic or pharmacologic properties. The high levels of sensitivity and specificity achieved with immunoassays result from the specific, high-affinity, reversible binding of antibodies and antigens, and from the existence of methods for attachment of sensitive detectable labels (radioactive isotopes, fluorophores, ferritin, free radicals, bacteriophages and enzymes) to antibodies or antigens. Enzymes are most commonly used today.

Immunoassay techniques are based upon the complex binding of the antigenic substance being assayed (analyte) with an antibody or antibodies in which one or the other member of the complex may be labeled, permitting the detection and/or quantitative analysis of the target substance by virtue of the label activity associated with the labeled antigen complex or antibody. Immunoassays are generally classified into two groups: the heterogeneous immunoassay in which a labeled antigen or antibody is separated from the labeled antigen-antibody complex before measurement of label activity in either fraction; and the homogeneous immunoassay in which the activity of labeled antigen is measured in the presence of labeled antigen-antibody complex.

Two such diagnostic assay techniques used to determine the presence or amount of antigen in body fluids are generally known as "competitive" assays and "non-competitive" or "sandwich" assays. Typically, in "competitive" assay techniques, an unlabeled antibody or antigen preparation bound to a solid support or carrier is first reacted with a labeled antigen or antibody reagent solution and then with the body fluid sample wherein the antigen or antibody in the sample competes with the labeled antigen for sites on the supported antibody or antigen. The amount of labeled antigen reagent displaced indicates the quantity of antigen present in the fluid sample to be detected.

In the case of a "sandwich" or "non-competitive" assay, a quantity of unlabeled polyclonal or monoclonal antibody or antigen bound to a solid-support or carrier surface, is reacted with a body fluid sample being evaluated for antigens or antibodies, and then, after suitable incubation time and washing, the sample is further incubated with a solution of labeled anti-antibody. The labeled antibody bound to the solid phase in an antibody-antigen-antibody sandwich or the amount of unbound labeled antibody or antigen in the liquid phase would be determined as a measure of the presence of antigen or antibody in the test sample.

Thus the analyte can be an antibody or an antigen which has produced antibodies in the host.

The problem in the prior art is that some of the antibodies in samples recognize non-unique epitopes of proteins in the immunoassay and, thus, are non-specific. This can render the immunoassay non-specific. In the prior art this problem is referred to as "cross-reactivity". The result of cross-reactivity is that the immunoassay fails to accurately measure the specific analyte to be detected.

Various techniques have been used to prevent non-specific reactions with the analyte. A polyclonal antibody (derived by exposing an animal to the antigen and then separation of the antibodies from the blood serum) can be reacted with reagents which bind non-specific proteins for removal. Monoclonal antibodies (from a fusion of myeloma cells and cells of the animal which produce the monoclonal antibody) can be used to produce more specific binding. The monoclonal antibodies still do not necessarily block non-specific reactions where the antibody recognizes a common protein epitope of the biological sample to be tested. Various blocking agents containing proteins, such as milk or gelatin, are used to block non-specific sites which might cause the antibody to bind non-specifically. These help, but do not solve the problem.

The etiologic agent of equine protozoal myeloencephalitis (EPM) has been shown to be *Sarcocystis neurons*, (Dubey, J. P., et al., J. Parasitol. 77:212–218 (1991)). Similar neurological disease has been described in one horse due to Neospora spp. (Marsh, A. E., et al., J. Am. Vet. Med. Assoc. 209:1907–1913 (1996)). *S. neurona* utilizes the opossum (*Didelphis virginiana*) as its definitive host (Fenger, C. K., et al., J. of Parasitology 81:916–919 (1995); Fenger, C. K., et al., Vet. Parasitol. 68:199–213 (1997); Conference oft Research workers in Animal Diseases-Abstract 162, November 1997). The opossum passes infective sporocysts into the environment in its feces. Horses and ponies can become infected by ingesting sporocysts of *S. neurona* (Dubey, J. P, et al., J. Parasitol 77:212–218 (1991)), but they are dead end hosts. When the parasite enters the central nervous system of the horse, clinical neurological disease can result. No EPM cases have been reported in horses that have not originated from the Western Hemisphere. This is believed to be due to definitive host specificity of *S. neurona*, and therefore EPM does not typically occur outside the range of the opossum.

A Western blot test was developed to detect antibodies to *S.neurona*-specific antigens (approximately 22, 13 and 10.5 kilodaltons) (Granstrom, D. E., et al., J. Vet Diag Invest 5:88–90 (1993)) in cerebrospinal fluid of horses suspected of having EPM. In 1997, a different criteria for a positive test (with reactivity to proteins of approximately 13, 11, 10.5 and 10 kDa) was used by the same laboratory in the only published experimental infection study of Sarcocystis from opossums in horses (Fenger, C. K., et al., Vet Parasitol 68:199–213 (1997)). The Western blot test has also been used to estimate seroprevalence of antibodies to *S. neurona* in Pennsylvania, Ohio and Oregon (Bentz, B. G., et al., J. Am Vet Med Assoc 210:517–518 (1997); Saville, W. J., et al. JAVMA 210:519–524 (1997); Blythe, L. L., et al., JAVMA 210:525–527 (1997)). Seroprevalence estimates ranged from 22%–65% for various geographic regions sampled, suggesting high rates of infection with *S. neurona*. These Western blot assays have not been found to be reliable in predicting the presence of *Sarcocystis neurona* due to cross-reacting antibodies to other Sarcocystis sp. in the equine.

Recent work has indicated that immunodominant proteins of approximately 12 and 29 kDa are specific to *S. neurona* (Marsh, A. E., et al, J. Am Vet Med Assoc 209:1907–1913 (1996)), which would suggest a different criteria for a positive test result than that which has been used for diagnostic purposes and seroprevalence estimates. It was found that antibody cross-reactivity to other apicomplexian species can occur at or near these bands and therefore may cause false-positive test results.

SUMMARY OF THE INVENTION

The present invention relates to a method for the detection of *Sarcocystis neurona* in an immunoassay where a protein of *Sarcocystis neurona* is reacted with antibodies from an equine suspected of harboring the *Sarcocystis neurona* and the label is then detected, the improvement which comprises: reacting the protein of the *Sarcocystis neurons* with a non-labeled antibody to proteins of a Sarcocystis sp. other than the *Sarcocystis neurona* from a species of mammal other than equine prior to reaction with the antibody so that non-specific binding of the antibody is inhibited to thereby detect the *Sarcocystis neurona*.

The present invention relates to a method for the detection of disease caused by *Sarcocystis neurona* in equines which comprises:

(a) isolating fluid from the equine which can contain parasite induced antibodies to *Sarcocystis neurons* proteins, thus indicating the presence of the *Sarcocystis neurona*;

(b) reacting the fluid with at least one identifying antigen of the *Sarcocystis neurona* protein bound on a substrate, wherein the substrate has been blocked with antibodies to Sarcocystis sp. other than *Sarcocystis neurona* so that antibodies to *Sarcocystis neurona* antigen in the serum are bound to the identifying antigen;

(c) detecting the antibodies bound to the antigen so that the disease is detected.

Further, the present invention relates to a kit for the detection of disease caused by *Sarcocystis neurona* which comprises in separate containers:

(a) an identifying antibody which is specifically able to bind a first protein of *Sarcocystis neurona*; and (b) a non-labeled antibody which is specific for a second protein of a Sarcocystis sp other than *Sarcocystis neurona*.

Further still, the present invention relates to a kit for the detection of disease caused by *Sarcocystis neurona* in equines which comprises:

(a) a substrate with at least one identifying antigen to the *Sarcocystis neurona* bound on a surface of the substrate, (b) antibody to a Sarcocystis sp. other than *Sarcocystis neurons*; and (c) at least one reagent for detection of an antibody in a fluid of the equine which antibody binds to the antigen of *Sarcocystis neurons*.

OBJECTS

It is an object of the present invention to provide a highly reliable immunoassay method arid test kit for detecting antibodies in fluid from an equine which are developed as a result of infection by *Sarcocystis neurons*, the causative agent of protozoal myeloencephalitis in equines. In particular, it is an object of the present invention to provide a method and test kit which is relatively easy to perform, accurate and which is economical. These and other objects will become increasingly apparent by reference to the following description and the drawings.

DESCRIPTION OF PREFERRED EMBODIMENTS

Figure 1:
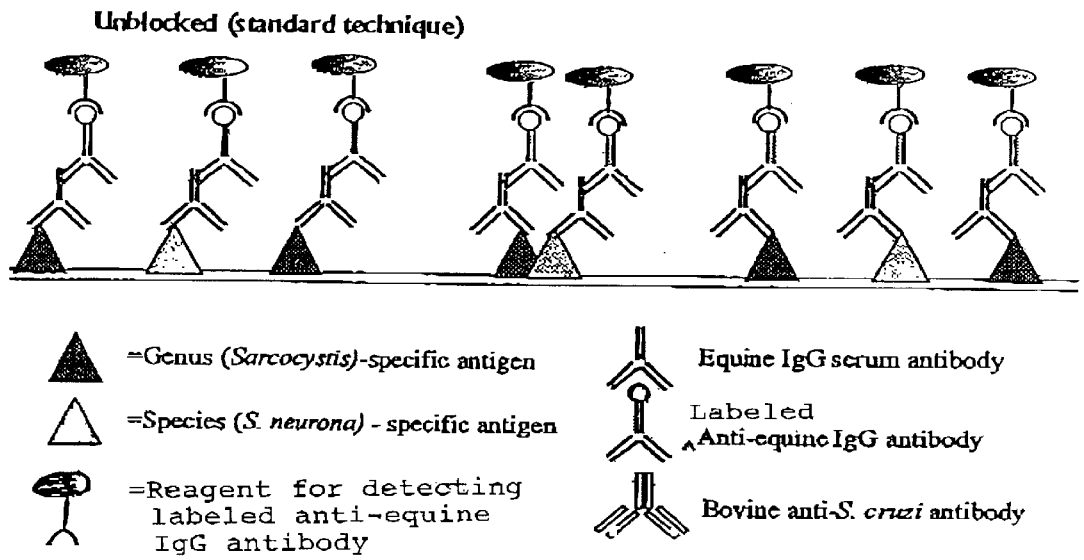
FIG. 1 is a schematic representation illustrating the non-specific binding of antigens using the method of the prior art. The schematic representation shows the membrane bound species (*S. neurona*)-specific antigen and genus (Sarcocystis)-specific antigen bound to the equine IgG serum antibodies against Sarcocystis. The bound equine IgG antibodies are then reacted with a labeled anti-equine IgG antibody which complexes with the equine IgG serum antibody. The labeled anti-equine IgG antibody complexed with the equine IgG serum antibody is detected with a reagent for detecting the labeled anti-equine IgG antibody.
Figure 2:
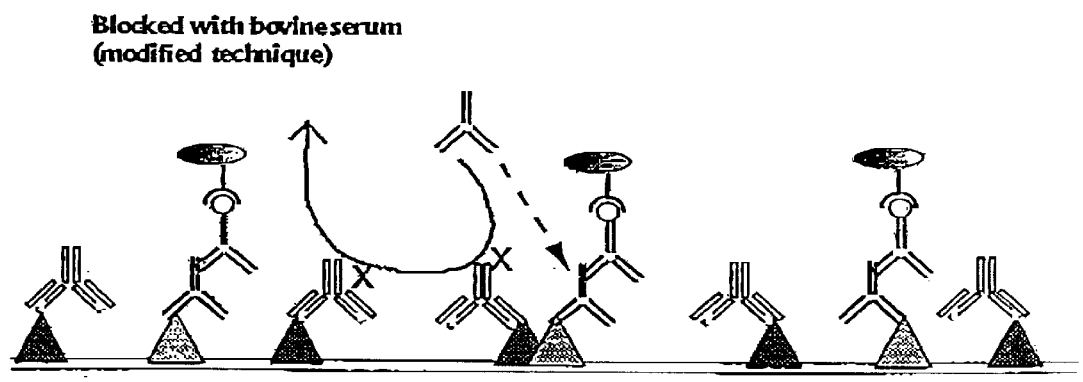
FIG. 2 is a schematic representation illustrating the specific binding of the antigens of *Sarcocystis neurona* using the method of the present invention. In the present invention, the membrane is preblocked with an antibody to a Sarcocystis sp. other than *Sarcocystis neurona* before reacting with the equine by IgG serum antibodies against Sarcocystis. The non-equine antibody binds the genus (Sarcocystis)-specific antigens and not the species (*S. neurona*)-specific antigens. Therefore, when the membrane is then reacted with the equine IgG serum antibodies, only the labeled anti-equine IgG serum antibodies bind the species (*S. neurona*)-specific antigens. When the membrane is then reacted with the labeled anti-equine IgG antibody, only the equine IgG serum antibodies bound to species (*S. neurona*)-specific antigens are detectable with the reagent for detecting the labeled anti-equine IgG antibody.

As used herein, the term "analyte" refers to the antibodies produced in an equine as a result of infection by an equine with *Sarcocystis neurona*. It is these antibodies which are to be measured. Typically the antibodies are measured from cerebrospinal fluid or serum.

The antibodies used in the present assay are preferably polyclonal and prepared in a conventional manner. The polyclonal antibodies are raised in a variety of domesticated animals, preferably a goat, and isolated from serum. The polyclonal antibodies are purified by affinity chromatography and then separated. While more expensive, monoclonal antibodies raised from hybridomas can be obtained in a conventional manner.

The preferred method of the present invention involves the separation of proteins (antigens) from the *Sarcocystis neurona* using gel electrophoresis and then transferring and binding the proteins to a membrane in a Western blot. The serum is reacted with the proteins on the membrane which are in bands and then the labeled polyclonal antibody is reacted with the analyte-antigen complex. Certain band or bands are selected for detection based upon the protein(s) selected for producing the polyclonal antibody in the horse during infection. It has been found that the 30 kDa and 16 kDa bands together provide a definitive result and thus are preferred based on testing statistically significant numbers of known positive and negative samples.

The important aspect of the present invention is that sites of the proteins selected for analysis are blocked with an antibody which does not occur in equines to another Sarcocystis sp. This prevents non-specific binding of the labeled antibody with epitopes of the analyte which are not definitive for *Sarcocystis neurona*.

It will be appreciated that other types of immunoassays are claimed where the antigenic protein from *Sarcocystis neurona* used to form the antibody antigen complex is reacted with an antibody from a non-equine directed against another Sarcocystis sp. All the available types of immunoassays are well known to those skilled in the art as previously discussed.

The following Examples 1 and 2 show the preferred embodiment of the present invention. There are many variations which can be used.

EXAMPLE 1

The purpose of this Example was to develop the most stringent criteria possible for a positive test result, and to estimate the sensitivity and specificity of the preferred EPM Western blot antibody test. The Example shows the ability of bovine serum with antibodies to *Sarcocystis cruzi*, which is non-infective in equines, to act as a blocking agent to prevent false positive results in the Western blot test for *S. neurons*.

Materials and Methods:

Selection of samples: 49 equine serum samples were obtained from India, where *S. neurona* is not known to exist and where there are no opossums. These samples were defined as known negative controls, because the horses could not possess antibodies to *S. neurona*. Serum and cerebrospinal fluid samples from 8 horses from which *S. neurona* was cultured postmortem were defined as known positive controls.

Culture of Antigen: Equine neural tissues from horses suspect for EPM were removed postmortem. The samples were stored in Hank's Balanced Salt Solution (HBSS) at room temperature. Within two hours of removal, portions of tissues were minced and ground in a Dounce homogenizer with cell culture medium. The slurry was poured onto confluent equine dermal cells and incubated at 37° C., 5% $CO_2$ for 24 hours. Medium was replaced after 24 hours and changed every two days for the first week and every week thereafter. One culture contaminated with an extracellular yeast resistant to amphotericin B at 1.25 $\mu$g/ml was kept viable by washing vigorously with HBSS six times, refeeding with media containing 4 $\mu$g/ml amphotericin B for 10 days before replacing with normal media (penicillin and amikacin concentrations kept the same). Viable, replicating merozoites of *S. neurona* were observed 7–49 days after inoculation.

Western blot testing: *S. neurons* merozoites were harvested from equine dermal cell culture and heat denatured in sample buffer (0.5 M Tris (pH 7.4) with 10% SDS, 20% Glycerol and 5% B-mercaptoethanol), all by volume. Denatured proteins were separated by SDS-PAGE in 12–20% linear gradient gels with a 4% stacking gel, both by volume. Separated proteins were electrophoretically transferred to Westran PVDF membranes (at 100 volts for 1½ hours, then 150 volts for ½ hour) and blocked overnight in blocking buffer 1% by volume bovine serum albumen (not infected with Sarcocystis) as a blocking agent for the control and 0.5% Tween-Tris Buffered Saline (blocking buffer). Blots were air-dried and frozen for later use.

For testing of serum samples according to the prior art, blots were wetted in 0.5% Tween-Tris Buffered Saline (TTBS) and clamped into a plexiglass press. Molecular weight markers were covered with blocking buffer in the first two lanes; the remaining 18 lanes were loaded with serum samples diluted 1:10 in blocking buffer, and incubated overnight. Subsequently, the blots were rinsed 3 times in TTBS, incubated for 3 hours in blocking buffer with biotin labeled goat anti-horse IgG (H+L), rinsed 3 times in TTBS, incubated in TTBS with avidin peroxidase conjugate for 45 minutes, rinsed 3 times in TTBS and developed with aminoethyl carbazole (AEC) stain.

For the bovine *S. cruzi* antisera treatment: The Western blot protocol was repeated with an additional treatment: the blots clamped in the plexiglass press were incubated with bovine serum with *Sarcocystis cruzi* antibodies in blocking buffer (1:10) for 2 hours, rinsed 3 times in TTBS, then loaded with equine samples and developed according to the prior art Western blot test.

Bovine *S. cruzi* antisera was tested by the Western blot protocol described above, using biotin labeled goat anti-equine IgG (H+L) to verify that anti-equine IgG would not bind to bovine IgG.

Data analysis: Known positive and negative samples were tested with and without the bovine *S. cruzi* antisera treatment. The protein bands detected by each sample were recorded and tested, alone and in combination with others, by the Fishers Exact test for independence (two-tailed). The combination of bands that was most strongly associated with a positive test was used to classify samples as Test Positives and Test Negatives. These totals were compared to the correct classification of True Positives and True Negatives, and test sensitivity and test specificity were calculated.

Results:

When tested by Western blot without the bovine *S. cruzi* antisera, no single band was significantly associated with *S. neurons* antibodies by the Fisher's Exact Test. This was also true of combinations of bands. Reactivity to proteins at 30 and 16 kDa occurred in all the culture-confirmed positive samples and in the majority of the known negative samples. No diagnostic criteria could be developed from these test results.

Analysis of the proteins detected by the culture-confirmed positives and known negatives on the bovine *S. cruzi* antisera treated blots showed the combined presence of the 30 and 16 kDa bands to be strongly associated by the Fisher's Exact test ($P>0.001$, two-tailed) with a positive test result.

All of the culture-confirmed positive samples exhibited both bands. 48 of the 49 known negatives tested negative by this criteria; one sample produced thin bands near enough to 30 and 16 KDa to be interpreted as a suspect positive. For the purposes of our analysis, that sample was classified as a false positive.

Bovine IgG directed against S. cruzi was not detected by the goat anti-equine IgG.

Sensitivity and specificity calculations: The diagnostic criteria of simultaneous reactivity to the 30 and 16 KDa bands used on bovine S. cruzi antisera treated blots was compared to the true status of the samples. Because the culture-confirmed positive samples were all correctly identified, the test sensitivity is estimated to be approaching 100%. 48 of the 49 known negatives were correctly identified, thus the test specificity is estimated to be approximately 98%. Using the presence or absence of S. neurona-specific antibodies as the outcome, the sample positive predictive value was 88.9%, and the sample negative predictive value was 100%.

|          | True (+) | True (−) | Totals |
|----------|----------|----------|--------|
| Test (+) | 8        | 1        | 9      |
| Test (−) | 0        | 48       | 48     |
| Totals   | 8        | 49       | 57     |

Example 1 supports earlier work which suggested that the best criteria for a positive S. neurona immunoblot test is immunodominant proteins at approximately 30 and 16 kDa (Marsh, A. E., et al., J. Am Vet Med Assoc 209:1907–1913 (1996)). The culture-confirmed positive samples used in this analysis were highly consistent in their reactivity to those specific proteins. The results of this example also demonstrates that the Western blot S. neurona antibody test can be subject to false positive results due to antibody cross-reactivity. This is not surprising, since a solid-phase immunofluorescence procedure (FIAX) used until 1993 in testing for EPM utilized the affinity of S. neurona-directed antibodies for S. cruzi (Diagnostic test offered by Oklahoma State University, Dr. Carl Fox Laboratory—Unpublished results). Additionally, S. cruzi antisera proved equally effective as S. neurona antisera for detecting S. neurona by avidin-biotin complex immunoperoxidase immunohistochemical staining (Hamir, A. N., et al., J. Vet Diagn Invest 5:418–422 (1993)). It is likely that antibodies directed against other common Sarcocystis species are a source of false positive tests.

Exposing S. neurona immunoblots to bovine S. cruzi antisera prior to testing equine samples proved to be an effective technique for reducing false positive test results. The bovine S. cruzi antibodies apparently bind to Sarcocystis genus-specific proteins, but not to S. neurona-specific proteins. Other Sarcocystis sp which horses may be exposed to include S. falcatula, S. rilei and others. By blocking the non-specific proteins that may be too close to discern from the specific proteins with the naked eye, both reading and interpretation is improved.

The sensitivity and specificity of the Western blot test was quite high. It is possible that a horse from which S. neurona is cultured will not have antibodies directed against the immunodominant proteins at 30 and 16 kDa. A false negative such as this could be due to acute onset of EPM, which has not allowed the animal sufficient time to mount a detectable antibody response. Clinical EPM testing done by the Michigan State University Animal Health Diagnostic Laboratory, East Lansing, Mich., has suggested that the protein at 30 kDa may be detected before the protein at 16 kDa during the course of seroconversion. A horse with acute clinical signs consistent with EPM, whose immunoblot test detects the 30 kDa band alone, should be retested after 7–10 days to confirm the antibody status of the animal. Another potential source of a false negative test may be a latent stage of S. neurona that does not stimulate an antibody response. Finally, the known negative samples from India appeared to provide many cross-reactive antibodies, but it is possible that further testing of sera from Eastern Hemisphere equids will reveal new possible sources of false positive test results.

Despite these sources of potential test error, the positive criteria and the blocking technique described here improves the specificity of the Western blot antibody test for S. neurona without any concurrent loss of sensitivity. They represent a highly stringent "gold standard". It is noteworthy that 2 of the 8 horses successfully cultured were also diagnosed with Wobbler's syndrome, and 1 of the 8 was diagnosed with leukoencephalomalacia (moldy corn poisoning). Without successfully culturing S. neurona from these animals with dual neurological problems, it would have been easy to classify them as false positives for S. neurona.

Finally, by classifying known positives and known negatives according to antibody status, rather than by clinical diagnosis of EPM or other neurological diseases, it is possible to evaluate the test solely by its ability to detect the desired antibodies.

EXAMPLE 2

The purpose of this experiment was to determine if pre-incubating the whole blots in bovine serum positive for antibodies to S. cruzi before drying and freezing gave the same result as blots treated as in Experiment 1.

Western blot testing: S. neurona merozoites were harvested from equine dermal cell culture and heat denatured in sample buffer (0.5 M Tris (pH 7.4) with 10% SDS, 20% Glycerol and 5% B-mercaptoethanol). Denatured proteins and molecular weight markers were separated by SDS-PAGE in 12–20% linear gradient gels with a 4% stacking gel. Separated proteins were electrophoretically transferred to Westran PVDF membranes and blocked overnight in 1% bovine serum albumen and 0.5% Tween-Tris Buffered Saline (blocking buffer). Blots were air dried and frozen for later use. For testing of serum samples, the blots were wetted in 0.5% Tween-Tris Buffered Saline (TTBS) and clamped into a Plexiglas press. Molecular weight markers were covered in B-TTBS (blocking buffer and serum albumin) in the first two lanes, the remaining 18 lanes were loaded with serum samples diluted 1:10 in blocking buffer and incubated overnight. Subsequently, blots were rinsed 3 times in TTBS, incubated for 3 hours in blocking buffer with biotin labeled goat anti-horse IgG (H+L), rinsed 3 times in TTBS, incubated in TTBS with peroxidase conjugate, rinsed 3 times in TTBS and developed with aminoethyl carbazole (AEC) stain.

Bovine S. cruzi Antisera Treatment:

Individual lanes: The Western blot protocol was repeated with an additional treatment; the blots were incubated with bovine serum with *Sarcocystis cruzi* antibodies in blocking buffer (1:10) for 2 hours, rinsed 3 times in TTBS, then loaded with equine samples and developed according to the previously described protocol.

Whole blots: The Western blot protocol was repeated. After the blots had blocked overnight, the blocking buffer was poured off. Bovine S. cruzi antisera was diluted 1:50 in blocking buffer and the blots were blocked with agitation in the solution for 1–1.5 hours, then air dried and frozen for later use. Equine samples were loaded and developed according to the previously described protocol.

Figures 3, 4:
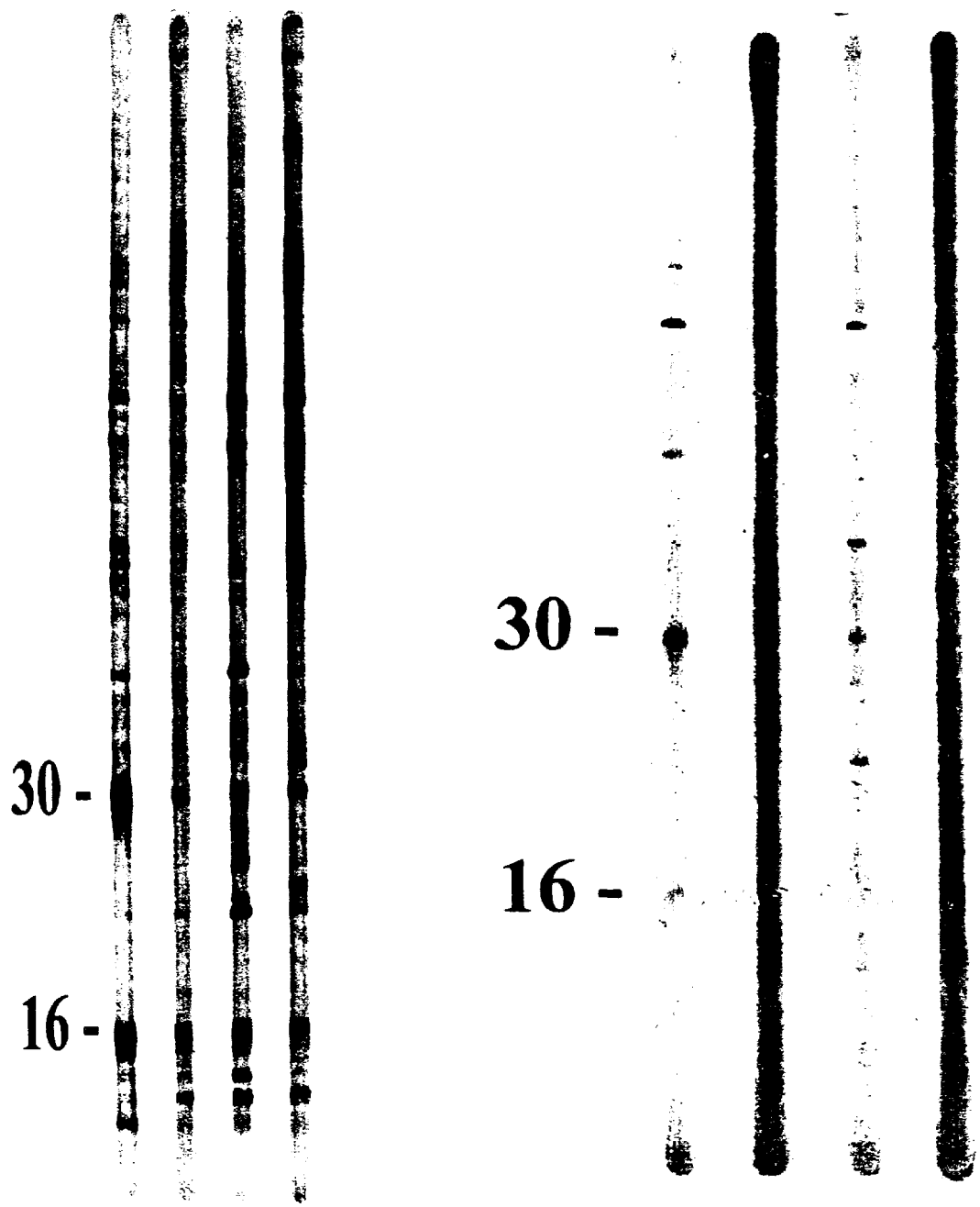
FIG. 3 is a Western blot prepared from *Sarcocystis neurons* merozoites, without bovine Sarcocystis sp. antibody treatment as shown in FIG. 1 according to the prior art. Lane 1—serum sample from culture-confirmed positive horse. Lanes 2–4—serum samples from Indian horses as negative controls.
FIG. 4 is a Western blot prepared from *S. neurona* merozoites. All lanes were blocked with bovine Sarcocystis sp. antibody treatment according to the present invention as shown in FIG. 2. Lanes 1–4—identical to samples used on the untreated blot of FIG. 3. Only the known positive sample (lane 1) detected proteins at both 30 and 16 kDa.

The results were the same as shown in Example 1 (FIGS. 3 and 4).

We claim:

1. A kit for the detection of disease caused by *Sarcocystis neurona* which comprises in separate containers:

(a) an identifying antibody which specifically binds to a 30 kDa protein of *Sarcocystis neurona* as determined by SDS-gel electrophoresis under denaturing conditions; and (b) a non-labeled antibody from a mammal other than an equine which is specific for a protein of a Sarcocystis sp. other than *Sarcocystis neurona*.

2. The kit of claim 1 which in addition contains in a further separate container the 30 kDa protein of *Sarcocystis neurona* which birds to antibodies from an equine suspected of harboring the *Sarcocystis neurona*.

3. A kit for the detection of disease caused by *Sarcocystis neurona* in equines which comprises:

(a) a substrate with at least one identifying antigen of the *Sarcocystis neurona* selected from the group consisting of a 16 kDa antigen and a 30 kDa antigen when separates by SDS-PAGE electrophoresis under denaturing conditions, bound on a surface of the substrate;

(b) antibody to a Sarcocystis sp. other than *Sarcocystis neurona* wherein the antibody is from a mammal other than the equine; and (c) at least one reagent for detection of an antibody in a fluid of the equine which antibody binds to the antigen of the *Sarcocystis neurona*.

4. The kit of claim 3 wherein the reagent is a labeled anti-equine antibody.

5. The kit of claim 4 wherein the label is biotin which is reacted with a biotin detecting reactant.

6. The kit of claim 3 wherein the substrate is used in a method selected from the group consisting of a Western blot and an ELISA.

7. The kit of claim 3 wherein the substrate is a gel.

8. The kit of claim 3 with a Western blot membrane as the substrate.

9. The kit of claim 3 including a biotin labeled goat anti-horse IgG' (H+L), peroxidase conjugate and aminoethyl carbazole which together provide the reagent.

10. The kit of claim 1 which in addition contains in a further separate container an identifying antibody which specifically binds to a 16 kDa protein of *Sarcocystis neurona* as determined by SDS-gel electrophoresis under denaturing conditions.

11. The Kit of claim 10 wherein addition contains in a further separate container the 16 kDa protein of *Sarcocystis neurona* which binds to antibodies from an equine suspected of harboring the *Sarcocystis neurona*.

12. The kit of any one of claim 1, 2, 10, or 11 wherein a user of the kit is instructed to first bind proteins of *Sarcocystis neurona* with the non-labeled antibody in the kit which is from a mammal other than an equine which is specific for a protein of a Sarcocystis sp. other than *Sarcocystis neurona*.

13. The kit of claim 3 wherein a user of the kit is instructed to first bind antigens of *Sarcocystis neurona* with the antibody in the kit which is from a Sarcocystis sp. other than *Sarcocystis neurona* and which is from a mammal other than the equine.

* * * * *

UNITED STATES PATENT AND TRADEMARK OFFICE
CERTIFICATE OF CORRECTION

PATENT NO. : 6,489,148 B1 Page 1 of 1
DATED : December 3, 2002
INVENTOR(S) : Linda S. Mansfield, Alice J. Murphy and Mary G. Rossano It is certified that error appears in the above-identified patent and that said Letters Patent is hereby corrected as shown below:

Column 2,
Line 43, "*Sarcocystis neurons*" should be -- *Sarcocystis neurona* --.
Line 5, "Conference oft" should be -- Conference of --.

Column 3,
Line 5, "also been)" should be -- also been --.
Lines 32 and 42, "*Sarcocystis neurons*" should be -- *Sarcocystis neurona* --.

Column 4,
Lines 2, 5, 12 and 49, "*Sarcocystis neurons*" should be -- *Sarcocystis neurona* --.
Line 9, "arid" should be -- and --.

Column 5,
Line 48, "*Sarcocystis neurons*" should be -- *Sarcocystis neurona* --.

Column 6,
Lines 8 and 57, "*Sarcocystis neurons*" should be -- *Sarcocystis neurona* --.

Column 9,
Line 19, "birds" should be -- binds --.
Line 27, "separates" should be -- separated --.

Signed and Sealed this

Eleventh Day of March, 2003

JAMES E. ROGAN
*Director of the United States Patent and Trademark Office*